US00PP28605P2

(12) United States Plant Patent
Hansen

(10) Patent No.: US PP28,605 P2
(45) Date of Patent: Nov. 7, 2017

(54) ***DIANTHUS* PLANT NAMED 'BLACK CHERRY FROST'**

(50) Latin Name: ***Dianthus* hybrid**
Varietal Denomination: Black Cherry Frost

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/330,911

(22) Filed: Nov. 14, 2016

(51) Int. Cl.
*A01H 5/02* (2006.01)

(52) U.S. Cl.
USPC ..... Plt./278

(58) Field of Classification Search
USPC ..... Plt./278
CPC ..... A01H 5/0233
See application file for complete search history.

*Primary Examiner* — Kent L Bell

(57) ABSTRACT

A new and unique cultivar of perennial carnation or pinks, *Dianthus* plant named 'Black Cherry Frost' with numerous, large, semi-double, lightly-fragrant flowers, on well-branched stems having up to 4 flowers per stem. Petals have coarse serrations and are velvety red with fine speckling and margin of light pink. *Dianthus* 'Cranberry Cocktail' has vigorous compact habit with gray-green foliage and does not require vernalization for flower production.

1 Drawing Sheet

Botanical denomination: *Dianthus* hybrid.
Cultivar designation: 'Black Cherry Frost'.

BACKGROUND OF THE INVENTION

The present invention relates to the new and distinct cultivar of carnation or pinks from the genus *Dianthus* and given the cultivar name 'Black Cherry Frost' previously known only internally by the breeder code 11-56-01. The new plant was the result of an intentional cross on May 16, 2011 by the inventor between *Dianthus* 'Starlette' U.S. Plant Pat. No. 21,438 as the female or seed parent and 'Pomegranate Kiss' U.S. Plant Pat. No. 21,895 as the male or pollen parent. The cross was harvested Jun. 21, 2011. The new hybrid was first isolated from trials at a wholesale perennial nursery in Zeeland, Mich. during the summer of 2012 as a single seedling and given the breeder number 11-56-01 during the remaining evaluation processes. *Dianthus* 'Black Cherry Frost' has been asexually propagated at the same nursery in Zeeland, Mich. since 2012 using traditional shoot tip cutting procedures and found to reproduce plants that are identical and exhibit all the characteristics of the original plant.

No plants of *Dianthus* 'Black Cherry Frost' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant.

Comparing the new plant to the female parent, 'Starlette', the new plant has lightly fragrant flowers with a darker red hue of the petals and a misting of lighter specks on the adaxial surface. Compared to the male parent, 'Pomegranate Kiss', the new plant has petals with tiny specks of between 0.1 and 0.3 mm diameter of a lighter pink with an occasional irregular splashed segment on velvety red base compared to the irregular splashed segments. Both 'Pomegranate Kiss' and 'Black Cherry Frost' have flower petals with a lighter pink margin. Other similar *Dianthus* include: 'Black Cherry Wild' U.S. Plant Pat. No. 21,893, and 'Double Spotty' U.S. Plant Pat. No. 13,884. *Dianthus* 'Black Cherry Wild' produces flowers with solid burgundy petals and not speckling, and *Dianthus* 'Double Spotty' produces flowers with a white spotting and petal margin.

*Dianthus* 'Black Cherry Frost' is distinct from its parents and all other *Dianthus* known to the applicant in the following combined traits:

1. Semi-double flowers opening up with a full and flat face.
2. Petals having a velvety red coloration with fine speckling of light pink.
3. Petal margin matches the light pink speckling.
4. Numerous flowers per peduncle with many flowers on heavily branched stems.
5. Large flower size producing a lightly sweetly spicy fragrance.
6. No vernalization required for flower production.
7. Floriferous, vigorous, with compact habit and finely-textured gray-green foliage.

BRIEF DESCRIPTION OF THE DRAWINGS

The photographs of the new invention are of a two-year-old plant in a full-sun trial garden and demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
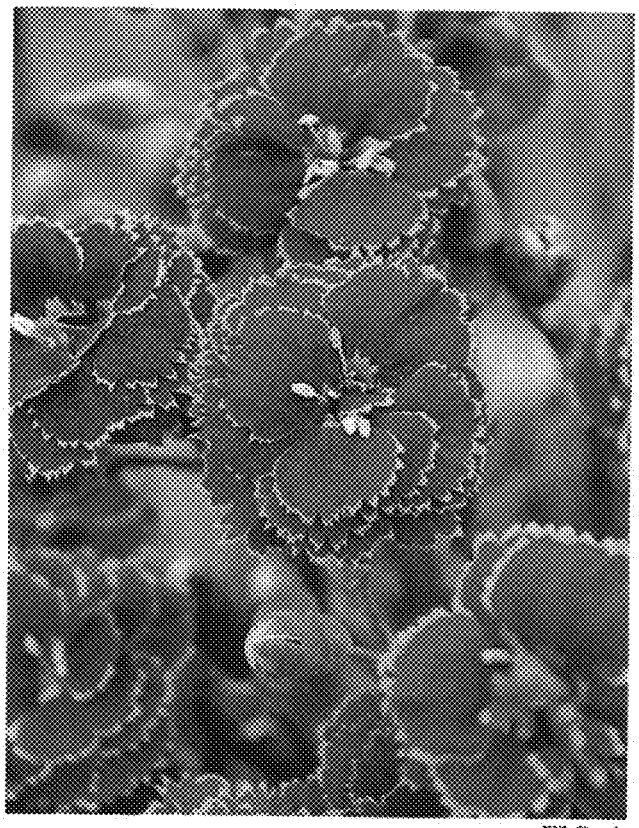
FIG. 1 shows a close-up of the flowers and buds.
Figure 2:
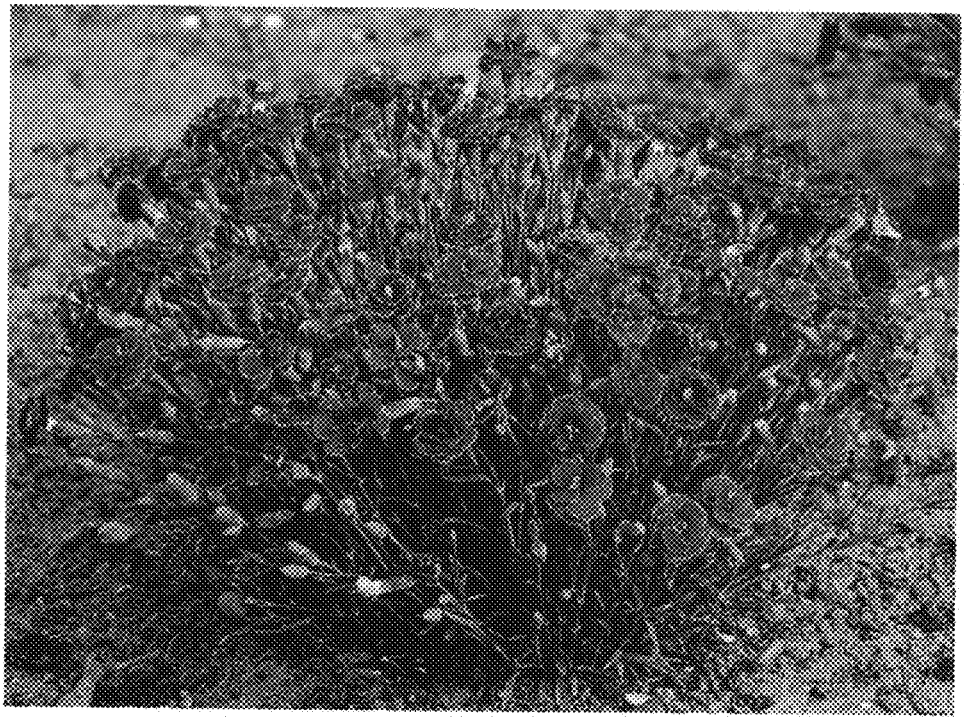
FIG. 2 shows the habit of the plant in mid-season flowering.

The following detailed description of the new plant is based on observations of one-year-old plants in greenhouse-grown containers in addition to two-year-old plants in full-sun trial garden at a nursery in Zeeland, Mich. with supplemental watering, light additions of fertilizer and free of other plant growth regulators. All color usage is in accordance with The 2001 edition of The Royal Horticultural Colour Chart except where common dictionary terms are used.

Botanical classification: *Dianthus* hybrid.

Parentage: 'Starlette' U.S. Plant Pat. No. 21,438 as the female or seed parent and 'Pomegranate Kiss' U.S. Plant Pat. No. 21,895 as the male or pollen parent.

Plant description:

*Habit*.—Caespitose, herbaceous, evergreen perennial; stems and peduncles branched, mostly erect stems; height of foliage about 15.0 cm and about 26.0 cm across; height in flower is about 25.0 cm.

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute apex; base decurrent, adpressed along stem and slightly perfoliate; no fragrance detected.

*Leaf dimensions*.—To about 6.5 cm long and about 5.0 mm wide, average about 6.0 cm long and 4.5 mm wide.

*Leaf color*.—Young expanding leaves abaxial nearest RHS 138B and adaxial between RHS N138B and RHS 139C; mature adaxial and abaxial nearest RHS 189B.

*Venation*.—Not pronounced; obscurely pinnate, coloration same as that of leaf top and bottom.

Stems: Upright; terete, glabrous, glaucous, branching at alternate nodes; about 18 per plant.

*Stem size*.—About 7.0 cm long before peduncle and about 4.0 mm wide at base.

*Stem color*.—Nearest RHS 145D.

*Branching*.—Numerous; typically alternate, from upper and lower leaf axils; about 11 per main stem and about 200 per plant; branch length average about 3.5 cm at time of initial flowering.

*Nodes*.—About 3.0 mm across; color nearest RHS 142C.

*Internodes*.—About 11 per stem before peduncle; average about 6.5 mm apart depending on growing temperature, shorter in cooler conditions.

Inflorescence:

*Type*.—Terminal, cymose; perfect; salverform; actinomophic; semi-double.

*Attitude*.—Upright to slightly outward.

*Dimension*.—About 4.0 cm across and extending about 34.0 mm above calyx tube.

*Flowers per stem*.—Three to four.

*Pedicel*.—Glaucous, glabrous, terete.

*Pedicel size*.—Terminal flower about 1.8 mm long and about 2.0 mm diameter; other flowers average about 25.0 mm long and 1.5 mm diameter.

*Pedicel color*.—Nearest RHS N138B.

*Flower bud one day prior to opening*.—Glaucous, glabrous, ellipsoid with rounded apex and rounded base.

*Flower bud size*.—One day prior to opening — about 2.5 cm long and about 8.0 mm wide at apex of calyx.

*Flower bud color*.—With petals exposed and still tight — petals darker than RHS 71A at apex and next to calyx nearest RHS 155D, calyx between RHS 138B and RHS 138C.

*Flower period*.—Beginning late spring and repeating in early fall if deadheaded; effective about four weeks per flowering season.

*Flower fragrance*.—Light, sweet spicy, clove-like.

*Flower lasting quality*.—About ten days on or cut from plant.

*Petals*.—Glabrous except pubescent in adaxial limb; about 15 per flower; consisting of a rounded blade or limb and a claw; limb and claw combined are obovate with long tapered claw; apex and margin with coarse irregular dentations 3.0 mm deep; limb bent outwardly in distal 15.0 mm to nearly a ninety degree angle creating a full flat face; claw tapering to attenuate base about 1.0 mm across; persistent.

*Petal color*.—Abaxial claw base nearest RHS 145D, mid-claw nearest RHS 145C, distal claw nearest RHS 69C; abaxial limb base nearest RHS 69C, distal limb between RHS 70A and RHS 70B; adaxial claw base nearest RHS 155A, mid-claw nearest RHS 145D, distal claw nearest RHS 69C; adaxial limb main portion darker than blend between RHS 59A and RHS 61A, limb margin and minute speckles between RHS 73A and RHS 73B.

*Petal dimension*.—Overall about 36.0 mm long, about 17. 5 mm across at widest portion of limb and about 16.0 mm long; claw about 20.0 mm long and about 1.5 mm across at base; limb margin about 1.0 mm wide and speckles between 0.1 and 0.3 mm diameter.

*Calyx*.—Glabrous, glaucous; margins entire to micropuberulent; consisting of five sepals with acute apex and fused base forming five-toothed corolla tube fused in about proximal 15.0 mm; individually about 19.0 mm long and about 4.5 mm across at distal fusion; campanulate to about 19.0 mm long and about 8.0 mm in diameter.

*Calyx color*.—Abaxial nearest RHS 189B with glaucous coating, nearest RHS 137A with bloom remove and apex translucent and nearest RHS N155D; adaxial nearest RHS 138B, margin nearest RHS N155D.

*Peduncle*.—Glabrous, glaucous, terete, stiff; about 11.0 cm lung and about 2.5 mm diameter at base; attitude mostly upright.

*Peduncle color*.—Nearest RHS N138B.

*Bracts*.—Two pairs, opposite, glaucous, glabrous; sessile, margin entire, broadly obtuse to deltoid with broadly acute apex; outer pair about 8.0 mm long and about 5.0 mm wide, inner pair about 7.0 mm long and about 6.0 mm across.

*Bract color*.—Both pairs abaxial and adaxial center and apex between RHS 136A and RHS 136B, margin translucent to nearest RHS 145D.

*Androecium*.—Ten stamens, typically not all fully formed. Filaments: about 22.0 mm long, less than about 1.0 mm diameter; color nearest RHS 155A. Anther: sagittate to irregular, dorsifixed; about 2.5 mm long and about 1.2 mm wide; color between RHS 156D and RHS158D. Pollen: not produced on all stamens; sparse; color nearest RHS 159C.

*Gynoecium*.—Single. Style: typically split in two just above ovary. Pistil: adaxial puberulent, glabrous abaxial; distally curved over 360 degrees in distal 9.0 mm; about 26.0 mm long and 1.0 mm diameter; color nearest RHS 72D. Stigma: slightly flattened abaxial to adaxial; puberulent; about 1.0 cm long and 1.0 mm wide; color nearest RHS 77A. Ovary: superior; ellipsoid-shaped; about 7.0 mm long and 4.0 mm wide; color nearest RHS 144A distally and RHS 145B proximally.

Fruit: Not observed.

Seed: Not observed.

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Black Cherry Frost' essentially as herein described and illustrated.

* * * * *